United States Patent [19]

Gupton et al.

[11] Patent Number: 5,047,542

[45] Date of Patent: Sep. 10, 1991

[54] PROCESS FOR PREPARING PYRIDINE CARBOXYLIC ACID ESTERS

[75] Inventors: B. Franklin Gupton, Virginia Beach; James H. Rea, Portsmouth, both of Va.; Werner H. Mueller, Corpus Christi, Tex.; John Saukaitis, East Greenwich, R.I.

[73] Assignee: Hoechst Celanese Corporation, Somerville, N.J.

[21] Appl. No.: 214,549

[22] Filed: Jul. 1, 1988

[51] Int. Cl.$^5$ ............................................. C07D 213/55
[52] U.S. Cl. .................................... 546/250; 546/319; 546/321

[58] Field of Search ........................ 546/250, 319, 321

[56] References Cited

U.S. PATENT DOCUMENTS 4,723,011  2/1988  Dochner, Jr. ....................... 546/250

Primary Examiner—Mary C. Lee
Attorney, Agent, or Firm—Depaoli & O'Brien

[57] ABSTRACT

A novel method is disclosed for the preparation of 2,3-pyridine-dicarboxylates by the reaction of a ketoester such as dimethyl oxalacetate with an $\alpha,\beta$-unsaturated aldehyde or ketone such as 2-ethylacrolein and at least 1 molar equivalent of ammonium salt in suitable solvent.

15 Claims, No Drawings

PROCESS FOR PREPARING PYRIDINE CARBOXYLIC ACID ESTERS

BACKGROUND OF THE INVENTION

Literature methods for preparing 5,6-dialkyl and 5,6-alkyl-arylpyridine-2,3-dicarboxylic acids and esters are limited and often require oxidation of alkyl or aryl substituents at positions 2 and 3 in order to obtain diacids. Recently there has been disclosed a method for the preparation of substituted and disubstituted pyridine-2,3-dicarboxylic acid esters and 2-alkyl nicotinates utilizing α-halo-β-ketoesters and α,β-unsaturated aldehydes or ketones in the presence of an ammonium salt. The use of α-halo-β-ketoesters is not desired due to the fact that such materials are usually costly and unstable.

DESCRIPTION OF THE PRIOR ART

Pertinent prior art is European Patent Application 220518 which was published on May 6, 1987. This published European Patent Application is assigned to American Cyanamid Company and on the face thereof indicates that priority is based on a U.S. application Ser. No. 791,671, filed Oct. 28, 1985, now U.S. Pat. No. 4,723,011.

U.S. Pat. No. 4,723,011 discloses preparation of substituted and disubstituted pyridine-2,3-dicarboxylates by the reaction of an α-halo-β-ketoester such as chlorodiethyloxalacetate (chloro-DOX) and an α,β-unsaturated aldehyde or ketone such as 2-ethyl acrolein in the presence of at least 2 molar equivalents of an ammonium salt in order to produce the desired compounds.

Although the method disclosed in the above-identified U.S. Pat. No. 4,723,011 is effective, nevertheless, because of the commercial importance of the compounds, particularly as useful intermediates for the preparation of herbicidal 2-(2-imidazolin-2-yl) nicotinic acids, esters and salts, any improvement in the process is of tremendous potential economic significance.

One disadvantage in using the method of said U.S. Pat. No. 4,723,011 is the fact that a halo-substituted ketoester is a more expensive starting material and the most common, namely chloro-DOX, is also not as stable as the non-halo-ketoesters, i.e., DOX. Another disadvantage to this process is the formation of chloride salts, which leads to waste water disposal problems and requires the use of significantly more expensive materials of construction.

SUMMARY OF THE INVENTION

It has now been found that substituted and disubstituted pyridine carboxylic acid esters, such as pyridine-2,3-dicarboxylic acid esters, can be prepared by the reaction of a β-ketoester, such as DOX, with an α,β-unsaturated aldehyde or ketone, such as 2-ethyl acrolein, in the presence of at least 1 molar equivalent of an ammonium salt. It should be immediately apparent that the reaction mechanism involved in the instant invention is different from the reaction mechanism involved in the process of U.S. Pat. No. 4,723,011.

As disclosed in said U.S. Pat. No. 4,723,011, the entire disclosure of which is incorporated by reference, pyridine-2,3-carboxylates are useful intermediates for the preparation of herbicidal 2-(2-imidazolin-2-yl) nicotinic acids, esters and salts such as those disclosed in European Patent Application Number 81103638.3, filed Dec. 1, 1981, as illustrated in the following diagram:

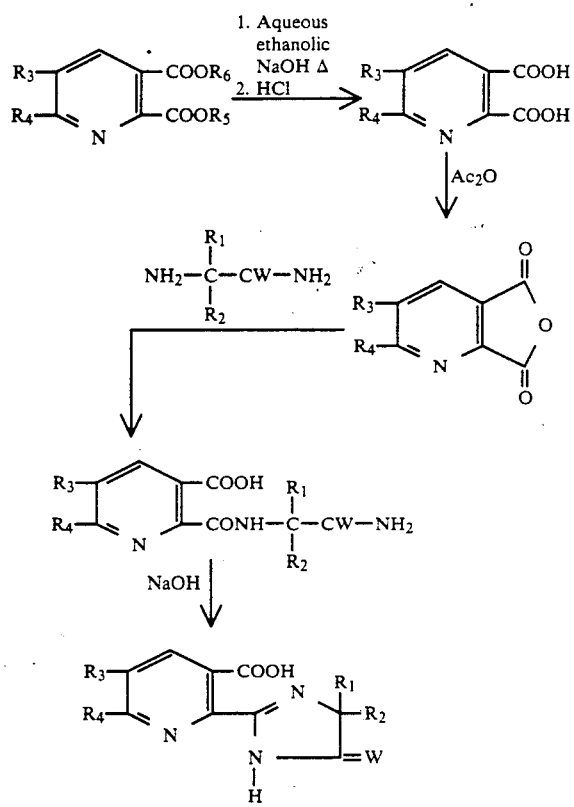

wherein $R_1$ is $C_1-C_4$ alkyl; $R_2$ is $C_1-C_4$ alkyl or $C_2-C_6$ cycloalkyl; and when R and R are taken together with the carbon to which they are attached they may represent $C_2-C_6$ cycloalkyl optionally substituted with methyl; W is O or S; and $R_2$ and $R_4$ are hydrogen, halogen $C_1-C_6$ straight or branched alkyl, alkenyl, or phenyl optionally substituted; $R_3$ and $R_4$ are each $C_1-C_4$ alkyl.

It is an object of this invention to provide a method for the preparation of substituted and disubstituted pyridine-2,3-dicarboxylic acid esters and 2-alkyl nicotinates utilizing β-ketoesters and α,β-unsaturated aldehydes or ketones in the presence of an ammonium salt.

CROSS REFERENCE TO RELATED APPLICATIONS

This application is related to application Ser. No. 07/163,252, filed Mar. 2, 1988, in the name of three of the four inventors of the instant application. Quite simply put, copending application 07/163,252, filed Mar. 2, 1988, is directed toward a method of producing the same compounds utilizing the same reagents as the instant application. The sole difference being that the earlier filed application requires the use of a dehydrogenation catalyst, whereas the process of the instant application does not require said dehydrogenation catalyst.

SUMMARY OF THE INVENTION

The present invention is a novel method for the preparation of substituted and disubstituted pyridine 2,3-dicarboxylates of formula I

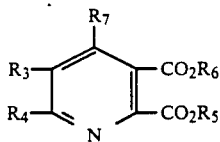

wherein $R_3$ is hydrogen, halogen, $C_1$-$C_6$ straight or branched alkyl, alkenyl, phenyl, or substituted-phenyl; $R_4$ and $R_7$ are each hydrogen, $C_1$-$C_6$ straight or branched alkyl, alkenyl, phenyl, or substituted-phenyl; $R_5$ and $R_6$ are each $C_1$-$C_4$ alkyl; comprising reacting a β-ketoester of formula II

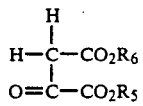

wherein $R_5$ and $R_6$ are defined above with an α,β-unsaturated aldehyde or ketone of formula III

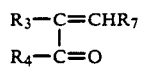

wherein $R_3$, $R_4$ and $R_7$ as described for in formula I above in the presence of a minimum of 1 molar equivalent of an ammonium salt in a solvent and at a temperature range of ambient temperature to the boiling point of the solvent until the reaction is essentially complete, as illustrated in the following reaction diagram:

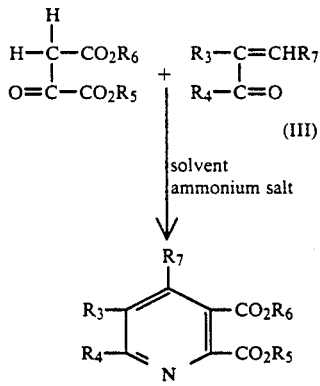

Solvents suitable for use in the method of this invention include: water, alcohols, chlorinated hydrocarbons, hydrocarbons, aromatic hydrocarbons, ethers, organic acids, esters, and aprotic solvents such as acetonitrile. The preferred solvents are lower alkyl alcohols, such as methanol, ethanol and propanol and aromatic hydrocarbons, such as benzene and toluene.

Thus, pyridine-2,3-dicarboxylic acid esters containing substituents in the 4-, 5- and 6-position may conveniently be prepared by admixing essentially equimolar amounts of a formula II ketoester and formula III α,β-unsaturated aldehyde or ketone with an ammonium salt in a suitable solvent, and stirring the resulting reaction mixture at a temperature in the range of ambient temperature to the boiling point of the solvent, and preferably at reflux, until the reaction is essentially complete and isolating the formed 4-substituted, 4-5-disubstituted, 4,6-disubstituted, 5-substituted, 6-substituted or 5-6-disubstituted pyridine-2,3-dicarboxylic acid esters by standard laboratory techniques such as extraction, evaporation or column chromatography.

The amount of ammonium salt is not narrowly critical and amounts of from about 1 to about 3 mols of ammonium salt per mol of said aldehyde or ketone can be employed. Preferred ranges are about 1–2 mols. It is to be understood that greater amounts of ammonium salts can be used, i.e., greater than 3 mols, but no advantage is gained.

The ammonium salts operable in the novel process of this invention are those which have sufficient solubility in the particular solvent employed. Examples include acetate, nitrate, sulfamate, chloride, sulfate, etc. Particularly preferred are the sulfamates and the acetates, especially when using low molecular weight alcohols as the solvent.

The mol ratio of the ester of formula II to the aldehyde or ketone of formula III is not narrowly critical and can range from about 1:3 to about 3:1. It is preferred to use approximately 1:1.3 molar ratios.

Additionally, the method of the present invention is suitable for the preparation of substituted nicotinates of formula IV below

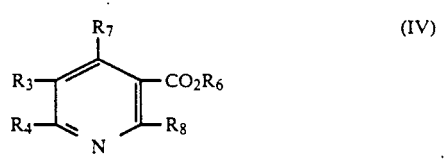

wherein $R_3$, $R_4$, $R_6$ and $R_7$ are as described for formula I; and $R_8$ is $C_1$-$C_4$ alkyl; comprising reacting a β-ketoester of formula V

wherein $R_4$ and $R_6$ are as defined for formula IV above, with an α,β-unsaturated aldehyde or ketone of formula III:

Formula IV nicotinates are also useful intermediates for the preparation of herbicidal 2-(2-imidazolin-2-yl) nicotinic acids, esters and salts by reaction with an aminocarboxamide in the presence of at least 3 equivalents of sulfur as described in U.S. Pat. No. 4,474,962 or by oxidation of $R_6$, for example, by the procedure described in U.S. Pat. No. 4,459,409, to yield the pyridine-2,3-dicarboxylic acid compounds of formula I above.

The following examples will illustrate the best mode contemplated for carrying out the novel process of this invention.

EXAMPLE 1

To a 1 liter, 3-neck Morton flask fitted with a thermowatch, reflux condenser, and motor-driven stirrer is added 94.0 grams (0.5 mols) of distilled diethyl oxalacetate (DOX), 68.4 grams (0.6 mols) of ammonium sulfamate, and 200.0 grams of methanol. The mixture is brought to reflux and held for 30 minutes, followed by the dropwise addition of 58.8 grams (0.7 mols) of distilled 2-ethacrolein over 30 minutes. Reflux temperatures maintained for an additional hour followed by cooling to about 10° C. and filtration.

There is obtained a yield of 46.19 grams of 5-ethylpyridine dicarboxylic acid diethyl ester, based on gas chromatography method, employing octanol as an internal standard and distilled 5-ethylpyridine dicarboxylic acid diester (5-EPDC) as a reference standard.

EXAMPLE 2

This example illustrates the process of the invention disclosed in copending application serial no. 07/163,252, filed Mar. 2, 1988, to a 1 liter, 3-neck Morton flask, filled with a thermowatch, reflex condenser, and a motor driven stirrer, is added 94.0 grams (0.5 mols) of distilled diethyloxalacetate (DOX), 0.4 grams of 5% palladium on carbon, 68.4 grams (0.6 mols) of ammonium sulfamate and 200 grams of methanol. The mixture is brought to reflux and held for 30 minutes, followed by the dropwise addition of 58.8 grams (0.7 mols) of distilled 2-ethacrolein over 30 minutes Reflux temperature is maintained for an additional hour, followed by cooling to about 10° C. infiltration. The yield of 5-EPDC was 53.18 determined on the same basis as in Example I.

As can be seen from a comparison of Example 1 and Example 2, the process of the earlier filed copending application results in a higher yield utilizing a catalyst. However, the process of the instant application still gives a very excellent yield of desired product in the absence of the catalyst, thereby possessing an economic advantage in that a catalyst is not required.

EXAMPLE 3

The procedure of Example 1 is repeated with the exception that 0.5 mols of ammonium acetate and 1.0 mols of acetic acid is utilized.

5-ethylpyridine dicarboxylic acid diethyl ester is obtained.

EXAMPLE 4

The procedure of Example 1 is repeated with the exception that ethanol is used as the solvent as opposed to toluene.

5-ethylpyridine dicarboxylic acid diethyl ester is obtained.

EXAMPLE 5

The procedure of Example 1 is repeated with the exception that 1.35 mols of ammonium sulfamate is employed instead of 0.6 mols.

5-ethylpyridine dicarboxylic acid diethyl ester is obtained.

EXAMPLE 6

The procedure of Example 1 is repeated with the exception that toluene is employed as opposed to methanol. 5-ethylpyridine dicarboxylic acid diethyl ester is obtained.

The procedure of Example 1 is repeated using the following in place of the DOX, and/or the 2-ethylacrolein.

TABLE

| EXAMPLE | ESTER | ALDEHYDE OR ESTER | PRODUCT |
| --- | --- | --- | --- |
| 7 | DOX | acrolein | pyridine-2,3-dicarboxylic acid, diethyl ester |
| 8 | DOX | 2-methylacrolein | 5-methylpyridine-2,3-dicarboxylic acid, diethyl ester |
| 9 | DOX | methyl vinylketone | 6-methylpyridine-2,3-dicarboxylic acid, diethyl ester |
| 10 | DOX | crotonaldehyde | 4-methylpyridine-2,3-dicarboxylic acid, diethyl ester |
| 11 | acetoacetic acid, ethyl ester | acrolein | 2-methylpyridine-3-carboxylic acid, ethyl ester |

TABLE-continued

| EXAMPLE | ESTER | ALDEHYDE OR ESTER | PRODUCT |
|---|---|---|---|
| 12 | DOX | (acrolein structure) | 6-phenylpyridine-2,3-dicarboxylic acid, diethyl ester |
| 13 | (ethyl benzoylacetate) | (acrolein) | 2-phenylpyridine-3-carboxylic acid, ethyl ester |
| 14 | (ethyl benzoylacetate) | (phenyl vinyl ketone) | 2,6-diphenyl-3-carboxylic acid, ethyl ester |
| 15 | (ethyl benzoylacetate) | (methyl vinyl ketone) | 2-phenyl-6-methylpyridine-3-carboxylic acid, ethyl ester |
| 16 | (ethyl formylacetate) | (phenyl vinyl ketone) | 6-phenyl-2-methyl-3-carboxylic acid, ethyl ester |

What is claimed is:

1. A method for the preparation of substituted and disubstituted pyridine-2-3-dicarboxylates of formula I:

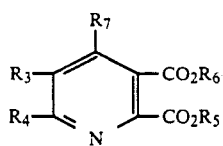

(I)

wherein $R_3$ is hydrogen, halogen, $C_1$-$C_6$ straight or branched alkyl, alkenyl, phenyl, or substituted-phenyl; $R_4$ and $R_7$ are each hydrogen, $C_1$-$C_6$ straight or branched alkyl, alkenyl, phenyl, or substituted-phenyl; and $R_5$ and $R_6$ are each $C_1$-$C_4$ alkyl; comprising reacting a β-ketoester of formula II:

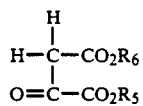

(II)

wherein $R_5$ and $R_6$ are defined above with an α,β-unsaturated aldehyde or ketone of formula III:

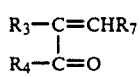

(III)

wherein $R_3$, $R_4$ and $R_7$ are as described in formula I in the presence of at least 1 molar equivalent of an ammomium salt in a solvent at a temperature range of ambient temperature to the boiling point of the solvent until the reaction is essentially complete.

2. A method according to claim 1 wherein the solvent is a lower alkyl alcohol.

3. The method of claim 2 wherein the solvent is methanol.

4. A method according to claim 2 wherein the ketoester is diethyl oxalacetate.

5. A method according to claim 1 wherein the aldehyde is 2-ethylacrolein.

6. A method according to claim 1 for the preparation of 5-substituted, 6-substituted and 5,6-disubstituted pyridine-2,3-dicarboxylic acid and esters.

7. A method according to claim 1 for the preparation of diethyl-5-ethylpyridine-2,3-dicarboxylate.

8. A method according to claim 1 for the preparation of diethyl 5-methylpyridine-2,3-dicarboxylate.

9. A method according to claim 1 for the preparation of diethyl-6-methylpyridine-2,3-dicarboxylate.

10. A method according to claim 1 for the preparation of diethyl-4-methylpyridine-2,3-dicarboxylate.

11. A method according to claim 1 for the preparation of diethyl-6-phenylpyridine-2,3-dicarboxylate.

12. A method according to claim 1 for the preparation of diethylpyridine-2,3-dicarboxylate 13. A method for the preparation of substituted nicotinates having the structure:

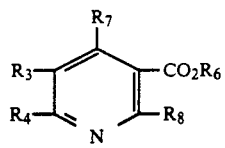

wherein $R_3$ is hydrogen, halogen, $C_1$-$C_6$ straight or branched alkyl, alkenyl, phenyl, or substituted-phenyl; $R_4$ and $R_7$ are each hydrogen, $C_1$-$C_6$ straight or branched alkyl, alkenyl, phenyl, substituted-phenyl; and $R_6$ and $R_8$ are each $C_1$-$C_4$ alkyl; comprising reacting the ketoester of formula V:

wherein $R_6$ and $R_8$ are as defined for formula IV, with an α,β-unsaturated aldehyde or ketone of formula III:

wherein $R_3$, $R_4$ and $R_7$ are as described in formula IV, in the presence of a minimum of 2 molar equivalent of an ammomium salt in an organic solvent at a temperature range of ambient temperature to the boiling point of the solvent until the reaction is essentially complete.

14. A method according to claim 10 for the preparation of 5-ethyl-2-methylnicotinate.

15. A method according to claim 10 for the preparation of ethyl-2-methyl-6-phenylnicotinate.

* * * * *